US006248934B1

(12) United States Patent
Tessier-Lavigne et al.

(10) Patent No.: US 6,248,934 B1
(45) Date of Patent: Jun. 19, 2001

(54) GENE TRAP VECTORS

(75) Inventors: Marc Tessier-Lavigne, San Francisco; William C. Skarnes, Berkeley; Kevin Mitchell, Albany; Philip A. Leighton, San Francisco, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/191,652

(22) Filed: Nov. 13, 1998

Related U.S. Application Data

(60) Provisional application No. 60/105,602, filed on Oct. 26, 1998.

(51) Int. Cl.[7] .......................... C12N 15/00; C12N 15/09; C12N 15/63; C12N 5/00
(52) U.S. Cl. ............................... 800/21; 800/22; 800/25; 800/18; 435/455; 435/320.1; 435/325; 435/69.1
(58) Field of Search ................ 435/455, 320.1, 435/325, 69.1; 800/12, 18, 21, 22, 25

(56) References Cited

U.S. PATENT DOCUMENTS 5,789,653 * 8/1998 Skarnes ..................................... 800/2
5,912,411 * 6/1999 Bujard et al. ............................ 800/2

OTHER PUBLICATIONS

Moreadith et al., Journal of Molecular Medicine, vol. 75, pp. 208–216, 1997.*
Seamark, Reproduction, Fertility, and Development, vol. 6, No. 5, pp. 653–657, 1994.*
Mullins et al., Journal of Clinical Investigations, vol. 98, No. 11, pp. S37–S40, 1996.*
Shirai et al., Zoological Science, vol. 13, pp. 277–283, Apr. 1996.*
Callahan et al., PNAS of the USA, vol. 91, pp. 5972–5976, Jun. 1994.*
New et al., Molecular Brain Research, vol. 37, pp. 317–323, Apr. 1996.*
Mombaerts et al., Cell, vol. 87, pp. 675–686, 1996.*
Stoykova et al., Developmental Dynamics, vol. 212, pp. 198–213, 1998.*
Steel et al., Hippocampus, vol. 8, pp. 444–457, 1998.*
Ito et al., Cell Tissue Research, vol. 290, pp. 1–10, 1997.*
Giniger et al., Roux's Archives of Developmental Biology, vol. 202, pp. 112–122.*
Gogos et al. Gene Trapping in a Differentiating Cell Lines: Regulation of the Lysosomal Protease Cathepsin B in Skeletal Myoblast Growth and Fusion. The Journal of Cell Biology. Aug. 1996, vol. 134, No. 4, pp. 837–847.
Baker et al. In Vitro Preselection of Gene–Trapped Embryonic Stem Cell Clones for Characterizing Novel Developmentally Regulated Genes in the Mouse. Developmental Biology. 1997, vol. 185, No. 2, pp. 201–214.

* cited by examiner

*Primary Examiner*—Jill D. Martin
(74) *Attorney, Agent, or Firm*—Richard Aron Osman

(57) ABSTRACT

The invention provides methods and compositions for expressing targeted gene products in vertebrate neurons. The compositions include gene trap vectors comprising a polynucleotide comprising promoterless selectable marker and axon reporter encoding sequences, which may be operatively joined to an internal ribosome-entry site, and may comprise a splice acceptor site located 5' to the selectable marker and axon reporter encoding sequences. The methods include methods of expressing an axon reporter in a cell by transferring the subject vectors into an embryonic stem cell and incubating the cell under conditions whereby the cell or a progeny of the cell differentiates into a neuron comprising an axon or dendrites, and the neuron expresses the axon reporter under the transcriptional control of the gene; and specifically detecting the axon reporter in the axon or dendrites. Neuronal specific expression may also be effected in disclosed binary systems.

22 Claims, 2 Drawing Sheets

GENE TRAP VECTORS

CROSS-REFERENCE TO RELATED APPLICATION

This application is a continuing application under 35USC120 of U.S. Ser. No. 60/105,602, filed Oct. 26, 1998.

INTRODUCTION

1. Field of the Invention

The field of the invention is gene trap vectors.

2. Background

Previous analyses of mutations in axon guidance molecules in vertebrates have been hampered by the lack of histochemical markers to selectively study particular axons among the mass of the neuropil (e.g. Baier et al., 1996; Serafini, et al., 1996). Analysis of the projections of neurons has been carried out using time-consuming dye-fill techniques, or existing histochemical markers which are limited mainly to widely-expressed antigens, such as TAG-1, which stains all commissural axons. Such labels do not permit one to visualize subpopulations of axons or to distinguish partially penetrant effects on many axons from fully penetrant effects on few axons.

Gene trapping in mouse embryonic stem cells offers a versatile and cost-effective approach to creating large numbers of insertional mutations that are immediately accessible to molecular characterization (Gossler et al., 1989; Friedrich and Soriano, 1991; Skarnes, Auerbach & Joyner, 1992; von Melchner et al., 1992). Activation of the reporter gene depends upon its insertion within an active transcription unit, thereby creating a mutation in the gene at the site of integration. The trapped gene can be sequenced rapidly using PCR-based methods (Townley et al., 1997) and the expression profile of the target gene can be readily determined by monitoring reporter gene activity in ES cell-derived chimeric embryos (Wurst et al, 1995) and/or in ES cell cultures following in vitro differentiation (Forrester et al., 1996). Thus, the advantage of the gene trap approach resides in the ability to pre-select insertional mutations of interest based on sequence and expression information prior to germline transmission and phenotype analysis.

A modification of the gene trap approach, the secretory trap (Skarnes, et al., 1995), allows one to recover selectively insertions into transmembrane or secreted protein-encoding genes, thus greatly enriching for mutations in genes expected to include axon guidance ligands and receptors. The secretory trap method has already been highly successful in identifying insertions into transmembrane or secreted genes expressed in the nervous system (Skarnes et al. 1995; Townley et al., 1997). In particular, LAR, netrin-1, neuropilin-2 and Semaphorin C, have already been implicated in axon guidance in mice and/or in other systems (reviewed in Tessier-Lavigne and Goodman, 1996).

We have developed a further modification of the gene trap approach to screen efficiently for genes involved in establishing correct patterns of neuronal connectivity in the mouse. This system utilizes a vector comprising both a gene trap module, in this case a secretory trap, and an axonal reporter to mark the axons of only those cells that normally express the trapped gene. Using this vector the trajectories of labeled axons can be compared between homozygous mutant and heterozygous mice to determine whether the trapped gene is required cell-autonomously for guidance of those axons. This method will also reveal whether the gene is involved in other aspects of nervous system development such as elaboration or pruning of axonal arbors or neuronal survival.

Relevant Literaure

A recent issue of the journal Developmental Dynamics was devoted to gene trap technology and included relevant articles by Voss et al. (1998) Dev Dynamic 212:171–180; Xiong et al. (1998) Dev Dynamic 212:181–197; and Stoykova et al. (1998) Dev Dynamic 212:198–213.

Ito K, Sass H, Urban J, Hofbauer A, Schneuwly S, (October 1997) Cell Tissue Res 290 (1): 1–10, describe the use of GAL4-responsive UAS-tau as a tool for studying the anatomy and development of the Drosophila central nervous system. Callahan C A, Thomas J B (Jun. 21, 1994) Proc Natl Acad Sci USA 91(13):5972–6 describe the use of a tau-beta-gal enhancer-trap transposon to study Drosophila neural development. Mombaerts et al. (1996) Cell 87, 675–686 describes the use of targeted mutagenesis to visualize an olfactory sensory map.

Relevant patent documents include Plasterk et al. (1997) WO97/29202, Mark et al. (1998) WO98/23933, Smith et al. (1994) WO94/24301, Ruley (1997) U.S. Pat. No. 5,627,058 and Skarnes (1998) U.S. Pat. Nos. 5,767,336 and 5,789,653.

SUMMARY OF THE INVENTION

The invention provides methods and compositions for identifying vertebrate genes and/or gene function required for correct wiring of the nervous system. The compositions include gene trap vectors comprising a polynucleotide comprising promoterless selectable marker and axon reporter encoding sequences, whereupon transfer into an embryonic stem cell and integration of the polynucleotide into a gene of the cell, the cell expresses the selectable marker and the axon reporter under the transcriptional control of the gene. In particular embodiments, the axon reporter coding sequence is operatively joined to the selectable marker by an internal ribosome-entry site, such that upon transfer into the cell, expression of the selectable marker and the reporter is detectable upon integration into an active transcription unit.

The invention provides several methods of expressing targeted gene products in neurons. In one embodiment the method comprises the step of transferring into a vertebrate embryonic stem cell vectors comprising a polynucleotide comprising promoterless selectable marker and axon reporter encoding sequences, under conditions whereby the polynucleotide integrates into the gene and the cell or a progeny of the cell expresses the selectable marker and the axon reporter under the transcriptional control of the gene.

In another embodiment, the method comprises the steps of (1) transferring into the embryonic stem cell a gene trap vector comprising a polynucleotide comprising promoterless selectable marker and axon reporter encoding sequences under conditions whereby the polynucleotide integrates into the gene and the cell expresses the selectable marker; (2) incubating the cell under conditions whereby the cell or a progeny of the cell differentiates into a neuron comprising an axon or dendrites, and the neuron expresses the axon reporter under the transcriptional control of the gene; and (3) specifically detecting the axon reporter in the axon or dendrites.

In another embodiment, specific expression of the targeted gene product in the neuron is achieved using a binary system. This method comprises the steps of (1) transferring into the embryonic stem cell a gene trap vector comprising a polynucleotide comprising promoterless selectable marker and transcription factor encoding sequences under conditions whereby the polynucleotide integrates into the gene and the cell expresses the selectable marker and transcription factor under the transcriptional control of the gene; (2)

transferring into the cell or a progeny of the cell a vector comprising a polynucleotide comprising a targeted gene product (such as an axon reporter) encoding sequence under the operative control of a transcriptional regulatory region (e.g. a promoter or operator sequence) activatable by the transcription factor; and (3) incubating the cell under conditions whereby the cell or a progeny of the cell differentiates into a neuron comprising an axon or dendrites, and the neuron expresses the targeted gene product under the transcriptional control of the gene, via the transcription factor. This system allows amplification of the axon reporter signal as well as creating a more versatile insertion which can be used to drive expression of any desired targeted gene under the operative control of the transcription factor.

Accordingly, the invention facilitates the identification of mutant phenotypes in the nervous system by including a cell-autonomous axonal marker, such as placental alkaline phosphatase (PLAP), in the vector, such that the projection patterns of neurons expressing the disrupted gene can be selectively visualized, in wild-type and mutant animals, by a simple histological stain such as for alkaline phosphatase activity (Fekete and Cepko, 1993; Fields-Berry, et al., 1992). This method supersedes the need for lipophilic dye injections, allowing more animals to be studied, and reveals subtle defects in the projection patterns of small subsets of axons which would be indistinguishable amongst the mass of neuropil without such a marker. Mice carrying these insertions provide useful new markers of axonal projections when crossed into existing mutant backgrounds.

The invention is applicable to a wide variety of vertebrate systems such as zebrafish, chick, Xenopus, mice, etc. using standard, existing techniques for insertional mutagenesis (e.g. retroviral insertion: Gaiano et al., 1996; direct DNA injection: Stuart et al., 1988, gene trapping technologies, etc.). In some species, such as zebra fish, the axon reporter itself can function as the selectable marker and living animals can be directly screened (i.e. selected) for expression of the reporter in axons to detect insertions in genes expressed in neurons.

DETAILED DESCRIPTION OF PARTICULAR EMBODIMENTS OF THE INVENTION

Figure 1:
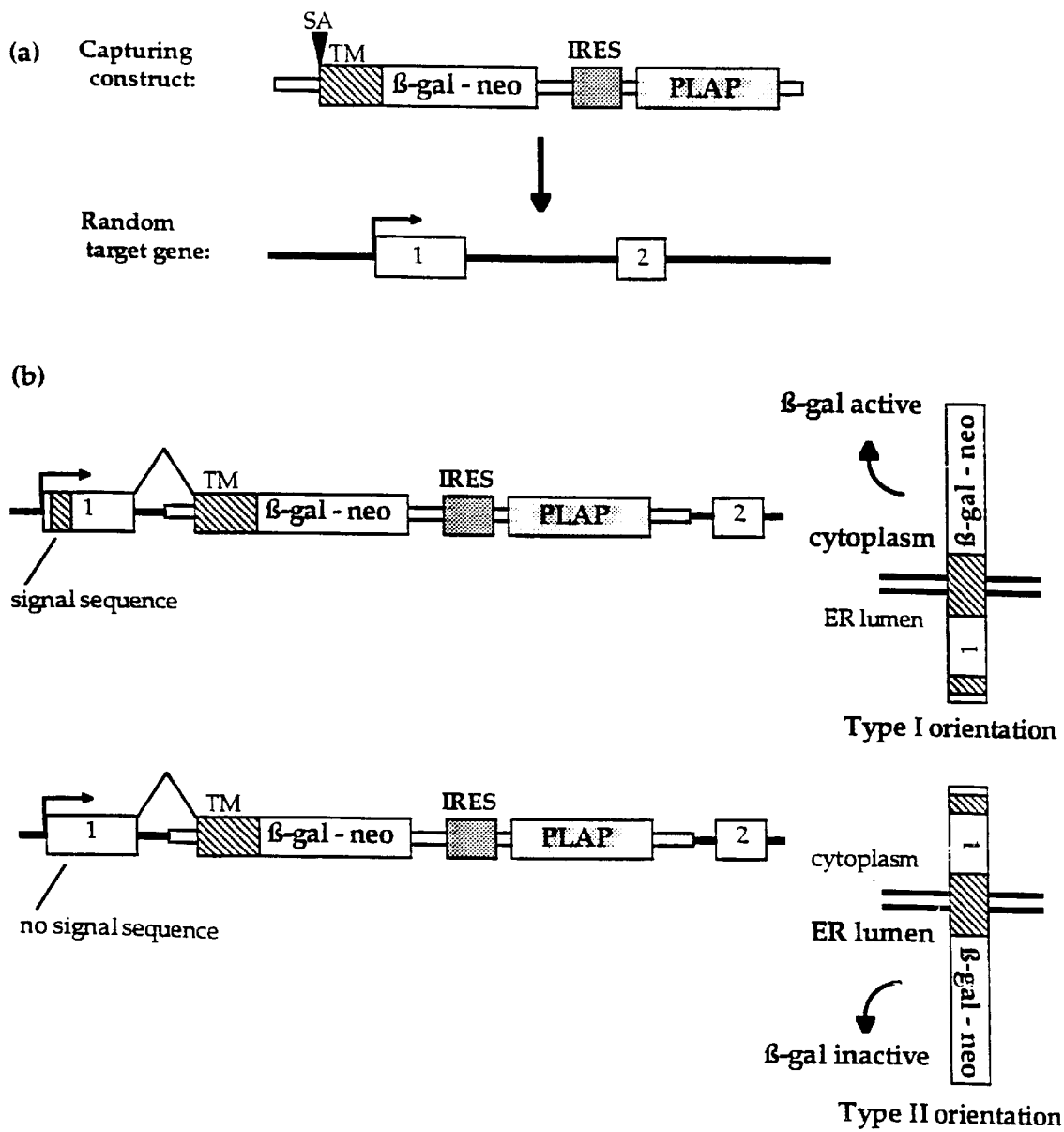
FIG. 1A. Schematic diagram of the PLAP secretory trap vector. The vector is shown here integrating into the intron of a random gene (between exons 1 and 2).
FIG. 1B. Schematic diagram of integrated PLAP secretory trap vectors providing alternatively, a type I orientation in the ER membrane having β-galactosidase activity, and a type II orientation, sequestering the β-galactosidase enzyme within the lumen of the ER, where it will be inactive.

The following descriptions of particular embodiments and examples are offered by way of illustration and not by way of limitation.

The subject gene trap vectors comprise a polynucleotide comprising promoterless selectable marker and axon reporter encoding sequences, whereupon transfer into a vertebrate, preferably mammalian, more preferably murine embryonic stem cell and integration of the polynucleotide into a gene of the cell, the cell expresses the selectable marker and the axon reporter under the transcriptional control of the gene. The term embryonic stem cell is intended to encompass pluripotent embryonic cells, such as fertilized and unfertilized egg cells, cells derived from blastula stage embryos, etc. A wide variety of selectable markers may be encoded, including fluorescent, nutrient, and especially, drug selectable markers. Preferred selectable markers provide for rapid, inexpensive and labor-minimized selection; most preferred are drug selectable markers such as neo, geo, hygro, and puro. Similarly, a wide variety of axon reporters may be encoded; essentially any gene product that is readily detected in axons and/or dendrites. Examples include alkaline phosphatases, tau-lacZ, tau-GFP, GAP43-GFP, etc. These coding sequences are functionally promoterless, meaning that when integrated in the cell, they are not under the transcriptional control of a vector-derived promoter.

In particular embodiments, the axon reporter coding sequence is operatively joined to a functional internal ribosome-entry site (IRES). A wide variety of IRES sites may be used. Factors to consider in selecting a suitable IRES site include the ability to effect high level translation, the ability to act constitutively in all cells, and the lack of an affect on transcriptional regulation. Exemplary suitable IRES sites include the encephalomyocarditis virus IRES (Mountford and Smith, 1995), the poliovirus IRES (Pelletier and Sonenberg, 1988), the aphthovirus IRES (Lopez de Quinto and Martinez-Salas, 1998), the hepatitis C virus IRES (Collier A J et al, 1998), or the IRES from the VEGF gene (Huez et al., 1998). In particular embodiments, the polynucleotide comprises the selectable marker and axon reporter encoding sequences in 5'-3' order, more particularly with a suitable IRES sequence positioned between the encoding sequences and operatively joined to the axon reporter encoding sequence.

In particular embodiments, the invention provides for neuronal specific expression of any targeted gene product, such as an axon reporter. Specific expression of the targeted gene product is achieved using a binary system. In this case the gene trap vectors comprise a polynucleotide comprising promoterless selectable marker and transcription factor encoding sequences, optionally operatively joined to a functional internal ribosome-entry site (IRES). Whereupon transfer into the embryonic stem cell and integration of the polynucleotide into a gene of the cell, the cell expresses the selectable marker and the transcription factor under the transcriptional control of the gene. Specific expression of the targeted gene product is achieved by introducing the targeted gene product encoding gene under the operative control of a transcriptional regulatory region (e.g. a promoter, enhancer and/or operator sequence) activatable by the transcription factor into the cell or a progeny of the cell. A wide variety of transcription factors can be used. Factors to include in selecting a suitable transcription factor include high-level and specific expression from the operator sequence in vertebrate cells, lack of cytotoxic or other phenotypic effects in vertebrate cells due to expression of the transcription factor alone, and sensitivity of the transcription factor to drugs, hormones, or other compounds which can be used to temporally control expression. Exemplary transcription factors include GAL4 (Brand and Perrimon, 1993) and the tet transactivator, tTA (Gossen and Bujard, 1992). A wide variety of targeted gene products may be expressed by these methods. For example, it may be desired to label the expressing neuron, e.g. with PLAP, GFP, etc. Alternatively, it may be desired to modify or even kill the expressing neuron, e.g. with a neuron growth or guidance factor or a toxin, such as diptheria toxin.

In particular embodiments, the polynucleotide comprises a functional splice acceptor site located 5' to the selectable marker and axon reporter encoding sequences. Factors to consider in selecting a suitable splice acceptor site include nucleotide sequences surrounding the splice site that promote efficient, consitutive splicing (branchpoint, splice site and splice enhancer elements). Exemplary suitable splice acceptor sites include those derived from the mouse En-2 gene and the adenovirus major late transcription unit (Gossler et al., 1989; Friedrich & Soriano, 1991).

In particular embodiments, the vector is fashioned as a secretory gene trap (e.g. Skarnes, 1998, U.S. Pat. Nos. 5,767,336 and 5,789,653). In such embodiments, the polynucleotide generally encodes a type II transmembrane domain and a lumen-sensitive marker, the expression of which produces a fusion protein wherein the transmembrane domain is positioned N-terminally to the lumen-sensitive marker. Hence, when the polynucleotide is expressed in the cell, the marker is differentially detectable if the gene encodes a secreted or membrane spanning protein having a signal sequence, e.g. detectable only if the gene encodes a secreted or membrane spanning protein having a signal sequence. Exemplary suitable type II transmembrane domains include those derived from the CD4 and ASGP membrane receptors.

A variety of gene trap designs may be used in the invention. An essential feature of the vector design is to ensure that the expression of the selectable marker/targeted gene product/axon reporter will depend on integration events within transcribed regions of the genome, preferably in protein-coding genes. For example, specific embodiments include plasmid- or retrotransposon-based vectors in which the selectable marker/axon reporter cassette is flanked by a splice acceptor site at the 5' side and a polyadenylation signal at the 3' side of the cassette. Such vectors are activated following insertion into introns of the target gene. Alternatively, the splice acceptor site may be omitted such that the vectors are activated upon insertion into exons of the target gene. A wide variety of methods are suitable for transferring the vector into the cell, depending on the nature of the vector, cell, etc. Examples include electroporation, viral infection, salt precipitation, microinjection, etc.

The invention provides several methods of expressing a targeted gene product in a cell. In one embodiment the method comprises the step of transferring into a vertebrate embryonic stem cell vectors comprising a polynucleotide comprising promoterless selectable marker and axon reporter encoding sequences, under conditions whereby the polynucleotide integrates into the gene and the cell or a progeny of the cell expresses the selectable marker and the axon reporter under the transcriptional control of the gene.

In another embodiment, the method comprises the steps of (1) transferring into a vertebrate embryonic stem cell a gene trap vector comprising a polynucleotide comprising promoterless selectable marker and axon reporter encoding sequences under conditions whereby the polynucleotide integrates into the gene and the cell expresses the selectable marker; (2) incubating the cell under conditions whereby the cell or a progeny of the cell differentiates into a neuron comprising an axon or dendrites, and the neuron expresses the axon reporter under the transcriptional control of the gene; and (3) specifically detecting the axon reporter in the axon or dendrites. In this embodiment, the selectable marker may be expressed under the transcriptional control of a vector or host cell borne promoter. The second incubation step may involve in vitro differentiation of cells in culture or in vivo differentiation in a chimeric or transgenic animal. The third detecting step involves specifically detecting the presence of the reporter in axons or dendrites of the neuron, as opposed to generally detecting the presence of the reporter in neuronal tissue, neurons, or neural cell bodies.

One application of the invention is a large-scale screen of the mouse genome for genes involved in axon guidance, using our modified version of the secretory trap. Including the cell-autonomous axonal marker, such as human placental alkaline phosphates (PLAP), in the vector enables the systematic analysis of the axonal phenotypes of a large number of mutant lines, a task that would otherwise be extremely time-consuming and difficult. The method is used to screen for trapping events in which PLAP-expressing axons are misrouted in homozygous mutant animals, indicating that the trapped gene encodes a protein (transmembrane, or more rarely, secreted) that is required cell-autonomously for guidance of axons.

In this example, the PLAP secretory trap vector is designed with the following elements (FIG. 1(a)): a promoterless fusion of a lumen-dependent marker (exemplifid with βgal) and selectable marker (exemplified with neomycin phosphotransferase) genes (βgeo) downstream of a functionally type II transmembrane domain (exemplifed with the transmembrane domain from CD4) and preceded by a suitable splice acceptor site (see, e.g. Skarnes, et al., 1995). Following these sequences is an internal ribosome entry site (IRES) and coding sequences for the PLAP gene. Upon insertion in ES cells into the intron of a gene, a βgeo fusion protein will be generated by splicing to the upstream exons of the endogenous gene. In cases where the upstream exons of the endogenous gene encode a signal sequence the fusion protein will adopt a type I conformation in the ER membrane which keeps the βgal enzyme in the cytoplasm where it is active. However, in fusions that lack a signal sequence the fusion protein adopts the opposite type II conformation in the membrane and the βgal enzyme is sequestered within the lumen of the ER where it is inactive (FIG. 1(b)). Thus, only insertions into genes encoding secreted or transmembrane proteins will generate an active βgal enzyme (Skarnes, et al., 1995). The PLAP protein will be translated independently from an internal ribosome entry site (IRES) sequence (Mountford and Smith, 1995), and will be targeted normally to the cell membrane, attached by a GPI-linkage (Fekete and Cepko, 1993; Fields-Berry, et al., 1992).

A prototype PLAP vector has been constructed and tested in ES cells. The PLAP secretory trap vector was electroporated into ES cells, which were then selected first with G418 (for neomycin phosphotransferase activity) and then (in replica plated colonies) for β-galactosidase activity. Cells from one line obtained in this way were stained for β-galactosidase activity (X-gal histochemistry) (blue reaction product) and for PLAP activity (purple reaction product) and found to possess both enzymatic activities. Surface expression of PLAP on these ES cells confirmed that translation from the IRES sequence works efficiently. Note that only a few cells from this clonal line express the trapped gene. This is commonly observed with the secretory trap vector (Skarnes et al., 1995) and reflects the fact that the trapped gene is expressed in differentiating ES cells and not undifferentiated ES cells. Compared to the original secretory trap vector, the PLAP vector yielded similar numbers of colonies and a similar proportion displayed a secretory pattern of βgal expression.

To further increase throughput, the method can employ a drug selection strategy providing a direct selection for insertions in secreted and membrane-spanning proteins, thereby avoiding the need for screening of such insertions based on detection of beta-galactosidase activity. For example, one approach is to modify the neomycin phosphotransferase gene such that it is inactive in fusions that adopt a type II orientation, e.g. engineer sites for N-linked glycosylation in the neo gene rendering neomycin phosphotransferase inactive upon exposure to glycosylation enzymes in the lumen of the ER (as with glycosylation of β-galactosidase when it transits through the ER). This approach obviates the need to replica plate each colony, and thereby increase throughput by as much as 10-fold. Furthermore, it provides more flexibility in the use of different axonal markers. In addition, other proven lacZ-based axonal markers like tau-lacZ and GAP-43-lacZ may be used where the ES cells are selected by means not involving lacZ.

The general steps of the screen are summarized as follows (see FIG. 2): 1. ES cells are transfected with the vector by electroporation, and secretory trap insertions selected on the basis of the β-gal staining pattern; 2. A sequence tag for each trapped gene is obtained using 5' RACE-PCR; 3. Inserts in genes of interest are injected into blastocysts; 4. Chimaeric males are backcrossed to produce heterozygous males, which are then bred to produce embryos for expression analysis, using PLAP histochemistry; 5. For those inserts with expression patterns in the nervous system, heterozygotes are intercrossed and the homozygous mutant phenotype analyzed using the PLAP marker. Exemplary experimental details of these steps are provided below.

1. Isolating secretory trap ES cell insertions: The vectors are transfected into ES cells by standard electroporation methods and the cells are replica-plated for βgal histochemistry. βgal-positive lines representing genuine insertions into genes with a signal sequence are readily distinguished from false positives by a diagnostic punctate subcellular βgal staining pattern. Using the original secretory trap vector, we have found an average of 20 genuine secretory trap events per electroporation and plating of 300 colonies. We alternate in successive electroporations between three vectors, each designed to read into the βgeo sequences in a different reading frame, in order to permit the widest survey of the genome.

2. Generating and analyzing the sequence: Sequence from the endogenous upstream exons fused to the βgeo gene can be obtained rapidly from the secretory trap lines using a method based on 5' RACE PCR, in which the amplified cDNA produced by 5' RACE is immobilized onto a solid substrate and cycle-sequenced directly, eliminating the need to clone the products before sequencing (Townley, et al., 1997). This method produces an average of 200 base pairs of sequence and as many as 40 lines may be conveniently processed in a week. These sequence tags are then used to search the rapidly burgeoning databases of known genes and expressed sequence tags (ESTs). In many cases this allows the identification of additional coding sequence and analysis for known motifs or homologies. We have found that roughly half of the genes associated with secretory trap events corresponded to known genes, one quarter matched ESTs, and one quarter were entirely novel. Inserts with homology to known genes involved in axon guidance or sequence motifs typical of receptor molecules are assigned a high priority for expression analysis, followed by novel genes in the order they arise.

While the majority of insertions are random, there also appear to be some hotspots for insertion, for instance, the LAR gene (Skarnes, et al., 1995). However, repeat events can be rapidly screened out on the basis of sequence, and, as long as new genes are being hit with each electroporation, this slight lowering of efficiency of the first step does not affect throughput. In fact, new insertions of the PLAP vector into some of the previously trapped genes are very useful in determining whether they have cell-autonomous functions in axon guidance.

Figure 2:
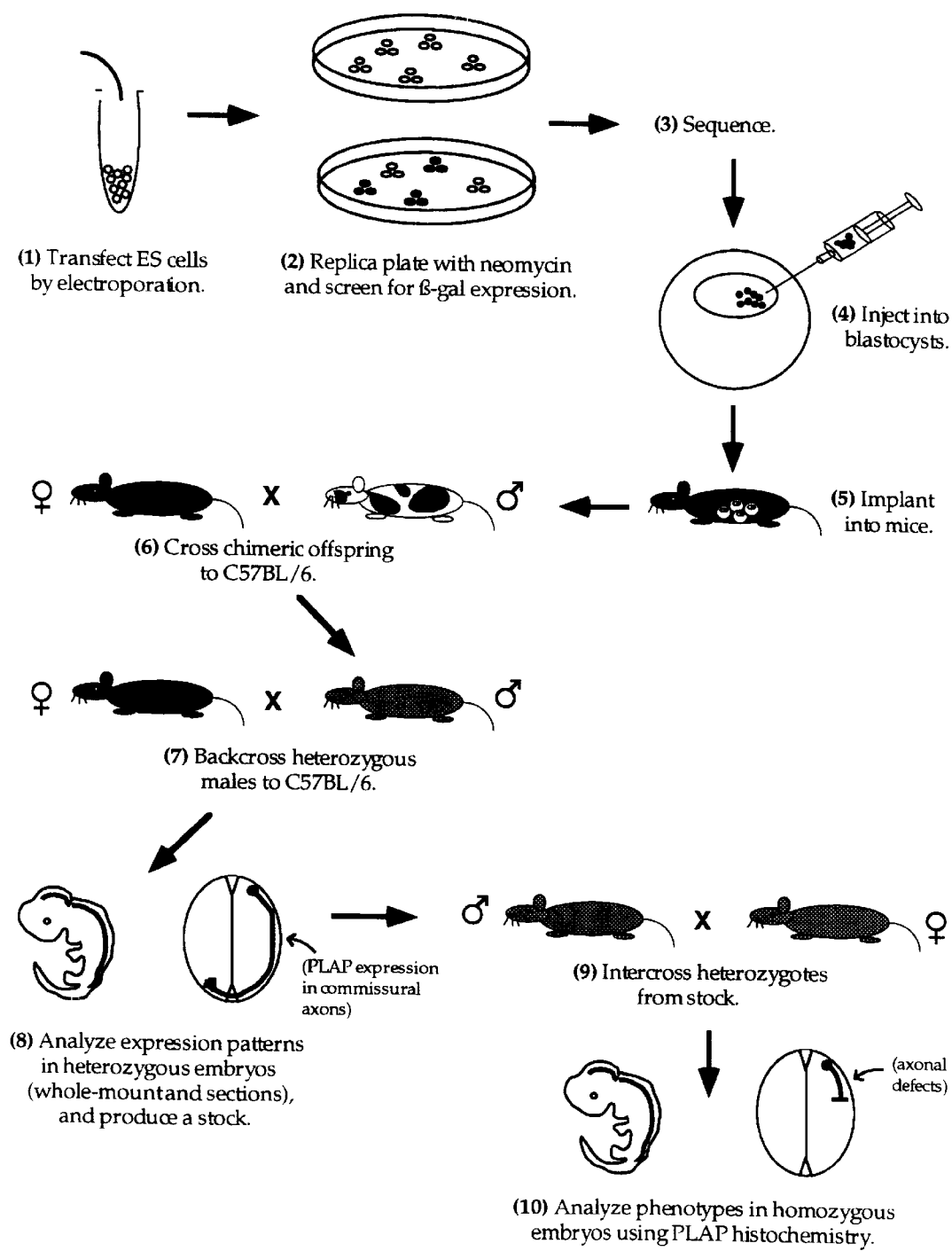
FIG. 2. Schematic diagram of the steps involved in the screen proposed here

3. Injecting blastocysts and passing insertions through the germline: We chose a feeder-independent ES cell line, CGR8.8, that gives a very high rate of transmission through the germline (1 germline male/5 blastocysts injected for >85% of clonal lines). To examine the expression patterns in mice we inject the cells into ten blastocysts for each line, implant these into pseudopregnant females, and allow the chimaeric pups to be born. Generally, 1–5 chimaeric males are produced which are backcrossed to C57BL/6 females to produce two heterozygous males. These males are used in timed matings to produce embryos for expression analysis, while simultaneously establishing a stock for analysis of homozygous mutant phenotypes (FIG. 2). Since a high proportion of the secretory trap insertions are expressed in the nervous system ($^{27}/_{35}$), this strategy is more efficient than the alternative approach of sacrificing chimaeric embryos to examine expression patterns at various stages and then reinjecting those lines found to be of interest. Genotyping is performed using a simple and reliable dot blot procedure which enables as many as 400 tail samples to be conveniently processed per day.

4. Staining for expression patterns: Embryos are collected and stained for PLAP activity in whole-mount and thick vibratome sections at two stages: E11.5, when axon tracts are being pioneered in the spinal cord; and E17, when cortical afferents and efferents are sending out projections, and when connections with lower brain structures are forming. Of particular interest are genes whose expression is restricted to discrete subsets of axons as these may encode receptors responsible for highly selective guidance decisions.

5. Phenotypic analysis in homozygous mutant embryos: For lines of interest we backcross the two males used above for expression analysis to C57BL/6 females to obtain male and female heterozygotes. These are intercrossed to generate homozygous embryos for phenotypic analysis. Embryos of the appropriate developmental stage (depending on the expression pattern from that insert) are collected, sectioned, and stained for PLAP expression. This allows a rapid examination of the axonal projections of the cells of interest and minimizes cage costs. Misrouting of the PLAP-expressing axons in homozygous mutant animals indicates that the trapped protein is required cell-autonomously for axon guidance, and might encode an axon guidance receptor, indicating further molecular characterization of the trapped gene, complemented by more detailed analysis of the mutant animals.

These insertions are found to generate null or severely hypomorphic alleles of the target gene, as the fusion proteins generated remain sequestered within the cell, rather than expressed on the cell surface (Skarnes et al., 1995). Approximately one third ($^{9}/_{28}$) of the secretory trap insertions were found to result in lethal phenotypes. It is possible that some low level of splicing around the insert may occur to generate wild-type message: this appears to have been the case in the netrin-1 knockout mouse (which nevertheless displayed a severe phenotype), (Serafini, et al., 1996). However, this may have been exceptional as no wild-type mRNA transcripts were observed for insertions in LAR or PTP6 (Skarnes, et al., 1995). Furthermore, the severity (time of death) of secretory trap insertions in fibronectin, agrin, and laminin B2 was similar to published null alleles generated by gene targeting, indicating that these insertional mutations effectively represent null alleles.

Elucidation of the function of trapped genes: Since identified genes encode signal sequence-bearing proteins and are required cell autonomously for axon guidance, many of them will encode axon guidance receptors. Also recovered are secreted factors required in autocrine fashion for guidance, e.g. Beaten Path protein of Drosophila (Fambrough and Goodman, 1996), and transmembrane proteins that function cell autonomously in axon guidance but are not themselves receptors for guidance cues, e.g., they simply have a structural role that ensures axonal integrity. All of these are of interest, and a next step in their analysis is to clone the ligand/receptor to which they bind. This can be accomplished by expression cloning using AP-fusion vectors, an approach that has recently been successful in a number of cases (e.g. He and Tessier-Lavigne, 1997).

Accordingly, one application of the disclosed modified PLAP secretory trap approach is to identify secreted and membrane-spanning proteins essential for axon guidance. The recovery of insertions in netrin-1, neuropilin-2 and semaphorin C has already demonstrated the validity of the secretory trap approach to access both secreted and membrane-spanning molecules relevant to this process. A second, but no less important application is to generate transgenic lines of mice in which specific axonal pathways are marked with PLAP. These marked lines are extremely useful reagents for deciphering the molecular mechanisms that control axon guidance and nerve regeneration. The method can also be applied to the identification of receptors involved in neuronal survival (as the labeled neurons should die in the homozygous mice), or in morphological differentiation of neurons, including in neuronal plasticity (as the morphology of the labeled neurons should be altered in the homozygous mice).

CITED REFERENCES

Baier, H, et al. (1996). Development 123, 415–25.
Brand, A. H. and Perrimon, N. (1993) Development 118, 401–15
Collier, A. J., Tang, S., and Elliott, R. M. (1998) J Gen Virol 79, 2359–66
Hicks G. G., Shi, E -G., Li, X -M., Pawlak, M., and Ruley, H. E. (1997). Nat. Genet. 16, 338–44.
Fambrough, D. and Goodman C. S. (1996). Cell 87,1049–58.
Fekete, D. M., and Cepko, C. L. (1993). Mol Cell Biol 13, 2604–13.
Fields-Berry, S. C., et al. (1992). Proc Natl Acad Sci USA. 89, 693–7.
Forrester, L. M., et al. (1996). Proc. Nat. Acad. Sci. USA 93, 1677–82.
Friedrich, G., and Soriano, P. (1991). Genes Dev 5, 1513–23.
Gaiano, N., et al. (1996). Nature 383, 829–32.
Gossen, M. and Bujard, H. (1992) Proc. Natl. Acad. Sci. USA 89, 5547–51.
Gossler, A., Joyner, A. L., Rossant, J., and Skarnes, W. C. (1989). Science 244, 463–5.
He, Z. and Tessier-Lavigne, M. (1997). Cell 90, 739–51.
Huez, I., et al. (1998) Mol Cell Biol 18, 6178–90
Lopez de Quinto, S. and Martinez-Salas, E. (1998) Gene 14, 51–6.
Mountford, P. S., and Smith, A. G. (1995). Trends Genet 11, 179–84.
Pelletier, J. and Sonenber, N. (1988). Nature 334, 320–325.
Serafini, T., et al. (1996). Cell 87, 1001–14.
Skarnes, W. C., Auerbach, B. A., and Joyner, A. L. (1992). Genes & Dev. 6, 903–18.
Skarnes, W. C., et al. (1995). Proc Natl Acad Sci USA. 92, 6592–6.
Stuart, G. W., McMurray, J. V., and Westerfield, M. (1988). Development 103,403–12.
Tessier-Lavigne, M., and Goodman, C. S. (1996). Science 274, 1123–33.
Townley, D. J., Avery, B. J., Rosen, B., and Skarnes, W. C. (1997). Genome Res 7, 293–8.
von Melchner, H., et al. (1992). Genes & Dev. 6, 919–27.
Wurst, W., et al. (1995). mice. Genetics 139, 889–99.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A gene trap vector comprising a polynucleotide comprising promoterless selectable marker and axon reporter encoding sequences, whereupon transfer of the gene trap vector into a mouse embryonic stem cell and integration of the polynucleotide into a gene of the cell, the cell expresses the selectable marker and the axon reporter sequences under the transcriptional control of the gene, and wherein expression of the axon reporter results in selective visualization of dendrite and axon projection patterns of neurons upon differentiation of the cell.

2. The gene trap vector of claim 1, wherein the axon reporter coding sequence is operatively joined to an internal ribosome-entry site.

3. The gene trap vector of claim 1, wherein the polynucleotide comprises a splice acceptor site located 5' to the selectable marker and axon reporter encoding sequences.

4. The gene trap vector of claim 1, wherein the polynucleotide encodes a type II transmembrane domain and a lumen-dependent marker, the expression of which produces a fusion protein wherein the transmembrane domain is positioned N-terminally to the lumen-dependent marker and whereupon transfer into the cell, expression of the lumen-dependent marker is differentially detectable if the gene encodes a secreted or membrane spanning protein having a signal sequence.

5. A method of expressing an axon reporter in a mouse embryonic stem cell, or a progeny cell thereof, comprising the step of:

transferring into a mouse embryonic stem cell or a progeny cell thereof the gene trap vector of claim 1 under conditions whereby the polynucleotide integrates into a gene of the cell, and wherein the cell expresses the selectable marker and the axon reporter under the transcriptional control of the gene and wherein expression of the axon reporter results in selective visualization of dendrite and axon projection patterns of neurons upon differentiation of the cell.

6. The method of claim 5, further comprising the step of: incubating the cell under conditions whereby the cell differentiates into a neuron comprising an axon or dendrites, wherein the neuron expresses the axon reporter; and
specifically detecting the axon reporter in the axon or dendrites.

7. The method of claim 5, wherein the axon reporter is selected from the group consisting of alkaline phosphatases, tau-lacZ, tau-GFP, and GAP43-GFP.

8. The method of claim 5, wherein the axon reporter is placental alkaline phosphatase (PLAP).

9. The gene trap vector of claim 1, wherein the axon reporter is selected from the group consisting of alkaline phosphatases, tau-lacZ, tau-GFP, and GAP43-GFP.

10. The gene trap vector of claim 1, wherein the axon reporter is placental alkaline phosphatase (PLAP).

11. A mouse embryonic stem cell, or a progeny cell thereof, made by integrating into the mouse embryonic stem cell a gene trap vector comprising a polynucleotide comprising promoterless selectable marker and axon reporter encoding sequences, wherein the polynucleotide is integrated into a gene of the cell, wherein the cell expresses the selectable marker and the axon reporter under the transcriptional control of the gene, and wherein expression of the axon reporter results in selective visualization of dendrite and axon projection patterns of neurons upon differentiation of the cell.

12. The cell of claim 11, wherein the cell is of a transgenic mouse whose genome comprises the integrated polynucleotide.

13. The cell of claim 11, wherein the axon reporter is selected from the group consisting of alkaline phosphatases, tau-lacZ, tau-GFP, and GAP43-GFP.

14. The cell of claim 11, wherein the axon reporter is placental alkaline phosphatase (PLAP).

15. A mouse embryonic stem cell, or a progeny cell thereof, made by integrating into a mouse embryonic stem cell a gene trap vector comprising a first polynucleotide comprising promoterless selectable marker and transcription factor encoding sequences, and a vector comprising a second polynucleotide comprising an axon reporter encoding sequence under the operative control of a transcriptional regulatory region activatable by the transcription factor, wherein the first polynucleotide is integrated into a gene of the cell, wherein the cell expresses the selectable marker and the transcription factor under the transcriptional control of the gene, wherein the expressed transcription factor activates the transcriptional regulatory region to express the axon reporter, and wherein expression of the axon reporter results in selective visualization of dendrite and axon projection patterns of neurons upon differentiation of the cell.

16. A method of using the mouse embryonic stem cell of claim 15 for production of a transgenic mouse, the method comprising:

introducing the mouse embryonic stem cell into a mouse embryo, implanting the embryo into a recipient mouse, allowing the embryo to develop to term, and identifying a transgenic mouse or producing a transgenic mouse by breeding, wherein the genome of the transgenic mouse comprises the integrated gene trap vector and axon reporter encoding sequence.

17. The cell of claim 15, wherein the axon reporter is selected from the group consisting of alkaline phosphatases, tau-lacZ, tau-GFP, and GAP43-GFP.

18. The cell of claim 15, wherein the axon reporter is placental alkaline phosphatase (PLAP).

19. A method of expressing an axon reporter in a mouse embryonic stem cell, or a progeny cell thereof, comprising the step of:

transferring into a mouse embryonic stem cell or a progeny cell thereof a gene trap vector comprising a first polynucleotide comprising promoterless selectable marker and transcription factor encoding sequences, and a vector comprising a second polynucleotide comprising a targeted gene product encoding sequence under the operative control of a transcriptional regulatory region activatable by the transcription factor, wherein the first polynucleotide is integrated into a gene of the cell, the cell expresses the selectable marker and the transcription factor under the transcriptional control of the gene, wherein the expressed transcription factor activates the transcriptional regulatory region to express the axon reporter, and wherein expression of the axon reporter results in selective visualization of dendrite and axon projection patterns of neurons upon differentiation of the cell.

20. The method of claim 19, further comprising the steps of:

incubating the cell under conditions whereby the cell differentiates into a neuron comprising an axon or dendrites, wherein the neuron expresses the axon reporter; and specifically detecting the axon reporter in the axon or dendrites.

21. The method of claim 19, wherein the axon reporter is selected from the group consisting of alkaline phosphatases, tau-lacZ, tau-GFP, and GAP43-GFP.

22. The method of claim 19, wherein the axon reporter is placental alkaline phosphatase (PLAP).

\* \* \* \* \*